United States Patent [19]
Stapleton et al.

[11] Patent Number: 5,374,532
[45] Date of Patent: Dec. 20, 1994

[54] **METHOD FOR DETERMINING SUSCEPTIBILITY TO *ESCHERICHIA COLI* URINARY TRACT INFECTIONS AND METHOD FOR DIAGNOSING SECRETORS AND NONSECRETORS**

[75] Inventors: Ann Stapleton; Edward Nudelman; Sen-itiroh Hakomori; Walter E. Stamm, all of Seattle, Wash.

[73] Assignee: The Biomembrane Institute, Seattle, Wash.

[21] Appl. No.: 936,400

[22] Filed: Aug. 31, 1992

[51] Int. Cl.$^5$ .................. G01N 33/53; G01N 33/566; G01N 33/569
[52] U.S. Cl. .................. 435/7.37; 435/7.21; 435/7.9; 435/7.92; 435/29; 435/960
[58] Field of Search ............ 435/7.21, 7.37, 7.9, 435/7.92, 960, 7.1, 7.2, 29; 424/11

[56] References Cited

U.S. PATENT DOCUMENTS 5,168,043 12/1992 Cordon-Cardo et al. ......... 435/7.23

OTHER PUBLICATIONS pap-2-Encoded Fimbriae Adhere to the P Blood Group-Related Glycosphingolipid Stage-Specific Embryonic Antigen 4 in the Human Kidney, Joan F. Karr et al., Infection and Immunity, Dec. 1990, pp. 4055–4062.

Stapleton et al. "Binding of Uropathogenic *Escherichia coli* R45 to Glycolipids Extracted from Vaginal Epithelial Cells is Dependent on Histo-Blood Group Secretor Status". J. Clin. Invest., 90:965–972 (Sep. 1992).

Stapleton et al. "Binding of Uropathogenic *Escherichia coli* to Glycolipids Extracted from Vaginal Epithelial Cells Collected from Nonsecretors and Secretors of Blood Group Antigens". Clin Res., 39(2):214A (Apr. 1991).

Sheinfeld et al. "Association of the Lewis Blood-Group Phenotype with Recurrent Urinary Tract Infections in Women", N. Eng J. Med., 320(12):773–777 (Mar. 23, 1989).

Leffler et al, "Glycolipid Receptors for Bacterial Adhesion on Human Urinary Tract Epithelium: Relation to Blood Group and Age" in Host Parasite Interactions in Urinary Tract Infections, pp. 93–99 (1989).

Lindstedt et al, "The Receptor Repertoire Defines the Host Range for Attaching *Escherichia coli* Strains that Recognize Globo-A". Infect. Immun., 59(3):1086–1092 (Mar. 1991).

*Primary Examiner*—Bidwell Carol E.
*Attorney, Agent, or Firm*—Sughrue, Mion, Zinn, Macpeak & Seas

[57] ABSTRACT

A method for determining susceptibility to *E. coli* urinary tract infection comprising assaying a sample of epithelial cells for the presence or absence of at least one of sialosyl galactosyl-globoside, disialosyl galactosyl-globoside and an extended globo structure carrying the same terminal epitopes as sialosyl galactosyl-globoside or disialosyl galactosyl-globoside, or assaying a sample of vaginal secretions for the presence or absence of at least one of sialosyl galactosyl-globoside or disialosyl galactosyl-globoside, and detecting the presence or absence of the at least one of sialosyl galactosyl-globoside, disialosyl galactosyl-globoside and the extended globo structure, a medicament comprising a biologically effective amount of at least one *E. coli* bacterial receptor analogue and a pharmaceutically acceptable diluent, carrier or excipient as well as a method for preventing *E. coli* urinary tract infection comprising administering to a host a biologically effective amount of at least one *E. coli* bacterial receptor or bacterial receptor analogue are disclosed.

6 Claims, 5 Drawing Sheets

METHOD FOR DETERMINING SUSCEPTIBILITY TO *ESCHERICHIA COLI* URINARY TRACT INFECTIONS AND METHOD FOR DIAGNOSING SECRETORS AND NONSECRETORS

FIELD OF THE INVENTION

The present invention relates to a method for determining susceptibility to *Escherichia coli* urinary tract infections and corresponding methods for diagnosing secretors and nonsecretors of histo-blood group antigens based on assaying vaginal epithelial cells, vaginal secretions and/or buccal epithelial cells. Also, the present invention relates to a method for preventing *E. coli* urinary tract infections as well as medicaments used for prevention of *E. coli* urinary tract infections. In particular, the present inventors have discovered the importance of disialosyl galactosyl-globoside for the determination of secretor status as well as preventing *E. coli* urinary tract inventions.

BACKGROUND OF THE INVENTION

Among the most common bacterial infections encountered in clinical practice are urogenital mucosal infections caused by *E. coli, Chlamydia trachomatis* and *N. gonorrheae* which are diagnosed and treated at a cost to society in the billions of dollars. These infections are frequently recurrent and efforts at prevention have been largely fruitless, in part because of the apparent ineffectiveness of the mucosal immune system. Mucosal immunity is short-lived and in the long term, not protective. Despite much effort, attempts to develop vaccines against these mucosal urogenital pathogens have not succeeded and even natural immunity does not protect against recurrent episodes of infection with these agents. In addition, antigenic variability of the organisms has complicated vaccine development.

In particular, acute uncomplicated urinary tract infections occur in millions of young women each year. While most of these women experience only single or sporadic infections, approximately 20% suffer very frequent ($\geq 3$/year) recurrences (Mabeck, C.E., *Postgrad. Med. J.*, 48:69–75, 1972). The apparent increased susceptibility to urinary tract infection in these patients cannot be explained by underlying functional or anatomic abnormalities of the urinary tract, but instead appears to arise from the interaction of infecting *E. coli* strains with these patients' epithelial cells.

Thus, women prone to frequent recurrences demonstrate prolonged colonization of the vaginal mucosa with *E. coli*, the predominant causative species in these infections, (Stamey, T.A. et al., *J. Urol*, 113:214–217, 1975) and three-fold more *E. coli* adhere to vaginal, buccal and uroepithelial cells from women with recurrent urinary tract infection than to cells from control patients (Schaeffer, A.J. et al., *N. Engl. J. Med.*, 304:1062–1066, 1981; Svanborg-Eden, C. et al., *Infect. Immun.*, 26:837–840, 1979). Women with a history of recurrent urinary tract infections are also more likely to be nonsecretors of histo-blood group antigens than are women without a history of infections (relative risk=3 to 4 (Kinane, D.F. et al., *Br. Med. J.*, 285:7–9, 1982; Sheinfeld, J. et al., *N. Engl. J. Med.*, 320:773–777, 1989; Hooton, T.M. et al., *Twenty-ninth Interscience Conference on Antimicrobial Agents and Chemotherapy*, 8, 1989 (Program and Abstracts); Lomberg, H. et al., *Infect. Immun.*, 51:919–926, 1986)), and *E. coli* adhere in greater numbers to uroepithelial cells from nonsecretors (Lomberg, H. et al., *Infect. Immun.*, 51:919–926, 1986).

*E. coli* adhesins also play an important role in the pathogenesis of urinary tract infection (Stapleton, A. et al., *J. Infect Dis.*, 163:773–779, 1989; Johnson, J.R., *J. Infect. Dis.*, 156:225–229, 1987; Jacobson, S.H. et al., *J. Infect. Dis.*, 152:426–427, 1985; Vaisenen, V. et al., *Lancet*, 2:1366–1369, 1981; Kallenius, G. et al., *Lancet*, 2:1369–1372, 1981; Vaisanen-Rhen, V. et al., *Infect. Immun.*, 48:149–155, 1984; Westerlund, B. et al., *J. Infect. Dis.*, 158:996–1002, 1988; Arthur, M. et al., *Infect. Immun.*, 57:303–313, 1989; Sandberg, T., B. Kaijser, *J. Clin. Microbiol*, 26:1471–1476, 1988; O'Hanley, P. et al., *N. Engl. J. Med.*, 313:414–420, 1985; Lidefelt, K.-J. et al., *Acta Paediatr. Scand.*, 76:775–780, 1987; Lund, B. et al., *Mol. Microbiol.*, 2:255–263, 1988), particularly the genetically related P and F adhesins.

P adhesins are present in 50% to 65% of *E. coli* strains causing cystitis (Stapleton, A. et al., *J. Infect Dis.*, 163:773–779, 1989; Arthur, M. et al., *Infect. Immun.*, 57:303–313, 1989; Sandberg, T., B. Kaijser, *J. Clin. Microbiol*, 26:1471–1476, 1988; O'Hanley, P. et al., *N. Engl. J. Med.*, 313:414–420, 1985; Lidefelt, K.-J. et al., *Acta Paediatr. Scand.*, 76:775–780, 1987; Lund, B. et al., *Mol. Microbiol.*, 2:255–263, 1988) and 75% to 90% of isolates from pyelonephritis (Johnson, J.R., *J. Infect. Dis.*, 156:225–229, 1987; Jacobson, S.Het et al., *J. Infect. Dis.*, 152:426–427, 1985; Vaisenen, V. et al., *Lancet*, 2:1366–1369, 1981; Kallenius, G. et al., *Lancet*, 2:1369–1372, 1981; Vaisanen-Rhen, V. et al., *Infect. Immun.*, 48:149–155, 1984; Westerlund, B. et al., *J. Infect. Dis.*, 158:996–1002, 1988; Arthur, M. et al., *Infect. Immun.*, 57:303–313, 1989; Sandberg, T., B. Kaijser, *J. Clin. Microbiol*, 26:1471–1476, 1988). The minimal receptor for the P adhesin is the galactose $\alpha 1-4$ galactose moiety, present in the globoseries glycolipids and the $P_1$ blood group antigen (Kallenius, G. et al., *FEMS Microbiol Lett.*, 7:297–302, 1980; Leffler, H. et al., *FEMS Microbiol. Lett.*, 8:127–134, 1980; Svanborg-Eden, C. et al., *Scand. J Infect Dis. Suppl.*, 24:144–147, 1980; Kallenius, G. et al., *Infection*, 8 (Suppl. 3):S288–S293, 1981; Kallenius, G- et al., *Lancet*, 2:604–606, 1981; Leffler, H. et al., *Infect Immun.*, 34:920–929, 1981; Kallenius, G. et al., *Scand. J. Infect. Dis. Suppl.*, 33:52–60, 1982; Svenson, S. B. et al., *Infection*, 11:73/61–79/67, 1983; Bock, K. et al., *J. Biol Chem.*, 260:8545–8551, 1985).

F adhesins are expressed in 30% to 65% of urinary tract infection isolates (Stapleton, A. et al., *J. Infect Dis.*, 163:773–779, 1989; Arthur, M. et al., *Infect. Immun.*, 57:303–313, 1989). The minimal binding moiety for the F adhesin is less well defined and probably more complex; proposed receptors include the Forssman and para-Forssman antigens, globoside, galactosyl globoside, globo A and globo H, and stage-specific embryonic antigen-4 (SSEA-4) (Lund, B- et al., *Mol. Microbiol.*, 2:255–263, 1988; Lindstedt, R. et al., *Infect. Immun.*, 57:3389–3394, 1989; Karr, J.F. et al., *Infect Immun.*, 58:4055–4062, 1990; Stromberg, N. et al., *EMBO J.*, 9:2001–2010, 1990). The globoseries glycolipids have recently been shown to be modified by the histo-blood group status, and ABH active globoseries GSLs are found in renal epithelium and in voided uroepithelial cells as well as on erythrocytes (Leffler, H. et al., *FEMS Microbiol. Lett.*, 8:127–134, 1980; Bock, K. et al., *J. Biol Chem.*, 260:8545–8551, 1985; Breimer, M.E. et al., *FEBS Lett*, 179:165–172, 1985; Breimer, M.E. et al., *J. Biochem.*, 98:1169-1180, 1985; Lindstedt, R. et al., *Infect. Immun.*, 59:1086-1092, 1991; Clausen, H. et al., *Vox Sang.*, 56:1-20, 1989; Kannagi, R. et al., *FEBS Lett.*, 175:397-401, 1984; Clausen, H. et al., *Biochem. Biophys. Res. Commun.*, 124:523-529, 1984).

Several lines of evidence have suggested that the increased susceptibility to recurrent urinary tract infection observed in some otherwise healthy women may be explained by genetic factors influencing the density and/or specificity of bacterial receptors available to mediate colonization of their uroepithelial cells (Schaeffer, A.J. et al., *N. Engl. J. Med.*, 304:1062-1066, 1981; Svanborg-Eden, C. et al., *Infect. Immun.*, 26:837-840, 1979; Kinane, D.F. et al., *Br. Med. J.*, 285:7-9, 1982; Sheinfeld, J. et al., *N. Engl. J. Med.*, 320:773-777, 1989; Hooton, T.M. et al., *Twenty-ninth Interscience Conference on Antimicrobial Agents and Chemotherapy*, 8, 1989 (Program and Abstracts); Lomberg, H. et al., *Infect. Immun.*, 51:919-926, 1986). Although it is known that nonsecretors of histo-blood group antigens are overrepresented among women with a history of recurrent urinary tract infections (Kinane, D.F. et al., *Br. Med. J.*, 285:7-9, 1982; Sheinfeld, J. et al., *N. Engl. J. Med.*, 320:773-777, 1989; Hooton, T.M. et al., *Twenty-ninth Interscience Conference on Antimicrobial Agents and Chemotherapy*, 8, 1989 (Program and Abstracts)) and that uroepithelial cells from nonsecretors show enhanced *E. coli* adherence compared with cells from secretors (Lomberg, H. et al., *Infect. Immun.*, 51:919-926, 1986), the biochemical basis for these observations has not been clarified.

SUMMARY OF THE INVENTION

Accordingly, an object of the present invention is to determine the biochemical basis for the overrepresentation of nonsecretors among women with a history of recurrent *E. coli* urinary tract infections. Another object of the present invention is to provide a method for determination of susceptibility to *E. coli* urinary tract infections as well as methods for diagnosing secretors and nonsecretors. Correspondingly, an object of the present invention is to provide a method for prevention of *E. coli* urinary tract infections as well as a medicament to prevent these urinary tract infections.

Accordingly, the present invention relates to a method for determining susceptibility to *E. coli* urinary tract infection comprising assaying a sample of epithelial cells for the presence or absence of at least one of Lewis$^a$ (Le$^a$), sialosyl galactosyl-globoside (sialosyl gal-globoside or SGG), disialosyl galactosyl-globoside (disialosyl gal-globoside or DSGG) and an extended globo structure carrying the same terminal epitopes as Le$^a$, SGG or DSGG or assaying a sample of vaginal secretions for the presence or absence of at least one of SGG or DSGG, and detecting the presence or absence of the at least one of Le$^a$, SGG, DSGG and the extended globo structure.

The present invention further relates to methods for diagnosing nonsecretor and secretor status, that is, a method for diagnosing secretors and nonsecretors of histo-blood group antigens comprising assaying a sample of vaginal epithelial cells, vaginal secretions or buccal epithelial cells for the presence or absence of at least one of SGG and DSGG and detecting the presence or absence of the at least one of SGG and DSGG and a method for diagnosing secretors of histo-blood group antigens comprising assaying a sample of vaginal epithelial cells or vaginal secretions for the presence or absence of at least one of globo H, globo ABO and lacto ABO, and detecting for the presence or absence of the at least one of globo H, globo ABO and lacto ABO.

The present invention also relates to a medicament comprising a biologically effective amount of at least one *E. coli* bacterial receptor analogue, and a pharmaceutically acceptable diluent, carrier or excipient as well as a method for preventing *E. coli* urinary tract infection comprising administering, to a host, a biologically effective amount of at least one *E. coli* bacterial receptor or bacterial receptor analogue.

BRIEF DESCRIPTION OF THE DRAWINGS

FIG. 1A depicts a representative autoradiogram of bacterial binding to glycosphingolipids (GSL's) and FIG. 1B depicts an orcinol-stained HPTLC of the samples.

DETAILED DESCRIPTION OF THE INVENTION

Figure 1:
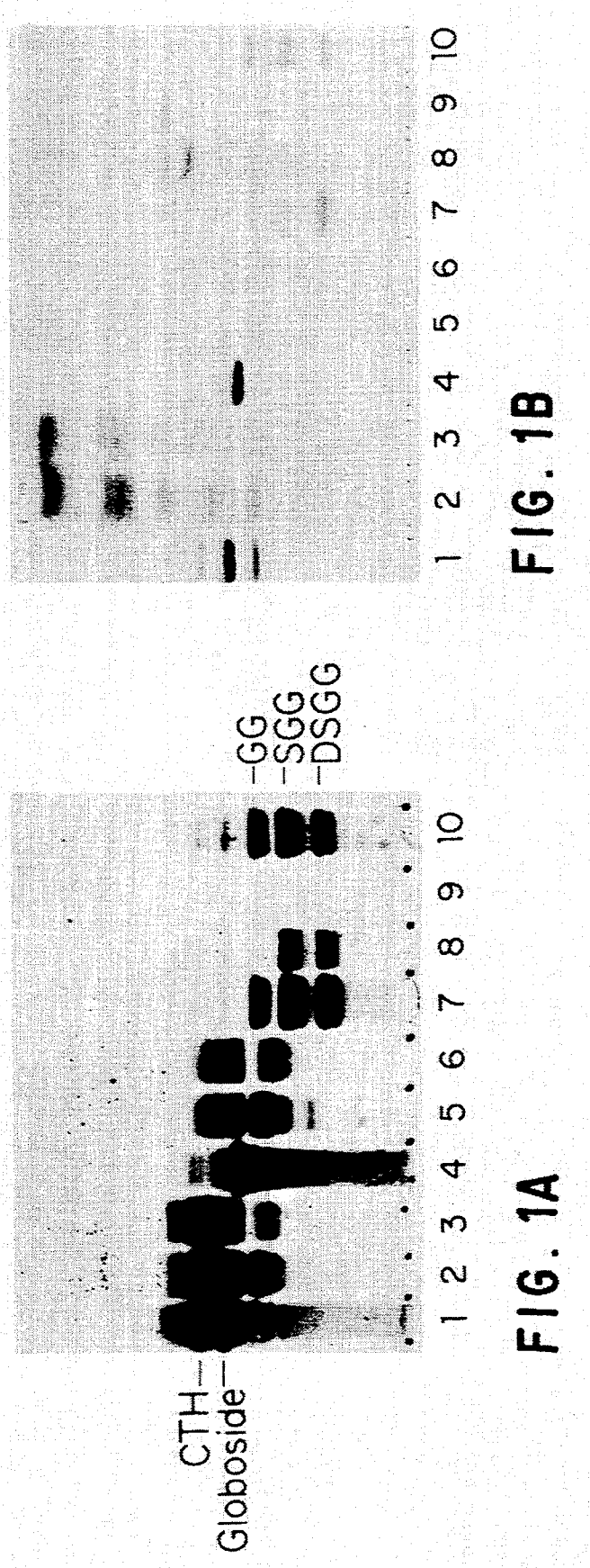
FIGS. 1A-1B show *E. coli* R45 binding to glycolipids extracted from vaginal epithelial cells.

Several lines of evidence have suggested that the increased susceptibility to recurrent urinary tract infection observed in some otherwise healthy women may be explained by genetic factors influencing the density and/or specificity of bacterial receptors available to mediate colonization of their uroepithelial cells (Schaeffer, A.J. et al., *N. Engl. J. Med.*, 304:1062-1066, 1981; Svanborg-Eden, C. et al., *Infect. Immun.*, 26:837-840, 1979; Kinane, D.F. et al., *Br. Med. J.*, 285:7-9, 1982; Sheinfeld, J. et al., *N. Engl. J. Med.*, 320:773-777, 1989; Hooton, T.M. et al., *Twenty-ninth Interscience Conference on Antimicrobial Agents and Chemotherapy*, 8, 1989 (Program and Abstracts); Lomberg, H. et al., *Infect. Immun.*, 51:919-926, 1986). Although it is known that nonsecretors of histo-blood group antigens are overrepresented among women with a history of recurrent urinary tract infections (Kinane, D.F. et al., *Br. Med. J.*, 285:7-9, 1982; Sheinfeld, J. et al., *N. Engl. J. Med.*, 320:773-777, 1989; Hooton, T.M. et al., *Twenty-ninth Interscience Conference on Antimicrobial Agents and Chemotherapy*, 8, 1989 (Program and Abstracts)) and that uroepithelial cells from nonsecretors show enhanced *E. coli* adherence compared with cells from secretors (Lomberg, H. et al., *Infect. Immun.*, 51:919-926, 1986), the biochemical basis for these observations has not been clarified. The present invention is based upon the experiments described below that show that nonsecretors express two unique GSL receptors for *E. coli*, SGG and DSGG, on their vaginal epithelial cells, which were not expressed in secretors' vaginal epithelial cells. SGG was accessible to binding by MAbs on the surface of the cells. Testing of the surface accessibility of DSGG to MAb binding could not be conducted because of the lack of an appropriate MAb.

In the experiments, the following methods were used.

Preparation of Glycolipids

Vaginal epithelial cells were collected from healthy female college students whose secretor statuses were determined using saliva hemagglutination inhibition assays and whose red blood cell Le$^a$ antigen phenotypes were determined using hemagglutination assays with an antibody to the Le$^a$ antigen (Hooton, T.M. et al., *Twenty-ninth Interscience Conference on Antimicrobial Agents and Chemotherapy*, 8, 1989 (Program and Abstracts)). Cells were collected by saline rinsing and gentle scraping with a spatula, were washed 4 times in phosphate buffered saline (PBS), pH 7.3 and were stored in a freezing medium (85% M199 (Sigma), 10% fetal calf serum, 5% DMSO) at −70° C. until use (Hooton, T.M. et al. , *Twenty-ninth Interscience Conference on Antimicrobial Agents and Chemotherapy*, 8, 1989 (Program and Abstracts); Daifuku, R. et al., *New Engl J. Med.*, 314: 1208–1213, 1986). Prior to glycolipid extraction, the cells were washed 4 times in PBS, quantitated in a hemocytometer and equalized for extraction procedures. The cells constituted a homogeneous population possessing typical morphology as viewed on light microscopy. 6 to 8×10$^7$ cells pooled from multiple patients or 10$^7$ cells/individual patient were used in each TLC assay. The total upper and lower phase glycolipid fractions were obtained as follows: cells were extracted twice with 10 volumes isopropanol:hexane:water (IHW) (55:25:20 by volume) with sonication in a warm bath and centrifugation at 2,500 RPM for 10 minutes. The combined supernatants were dried under nitrogen and twice resuspended in chloroform:methanol (CM) (2:1 by volume) with one-sixth volume water, inverted 20 times, and centrifuged at 2,000 RPM for 10 minutes (Folch, J. et al., *J. Biol Chem.*, 226:497–509, 1957). Total upper and lower phases were then evaporated under nitrogen stream and resuspended in IHW for chromatography.

For separation of total upper neutral glycolipids and gangliosides, upper phase glycolipids were first resuspended in 0.1% KCl in water, subjected to C18 Sep-Pak reverse phase column chromatography, washed with water, eluted with methanol, dried, and passed over a DEAE Sephadex A-25 column. Gangliosides were then eluted with 0.45M ammonium acetate in methanol, dried, and passed over a C18 column.

Glycolipids were preparatively separated by chromatography on glass HPTLC plates (Whatman) in chloroform:methanol:water (CMW) (50:40:10 by volume) with 0.05% CaCl$_2$. The bands were visualized with primuline under UV light, marked with a pencil, scraped from the silica plates, extracted twice in IHW, and dried. Glycolipid standards were isolated by known methods. To generate sialosyl gal-globoside, disialosyl gal-globoside standard was partially desialylated with 1% acetic acid at 100° C. for 5 to 10 minutes.

Bacterial Labelling

*E. coli* R45 was isolated from a woman with cystitis which had the pap family genotype, expressing both the P and F adhesins (Stapleton, A. et al., *J. Infect Dis.*, 163:773–779, 1989). Organisms were kept frozen in 50% glycerol/50% Luria broth (Maniatis, T. et al., *Molecular Cloning: A Laboratory Manual*, 1982) at −70° C. until the night before use, when they were streaked onto Luria agar plates (Maniatis, T. et al., *Molecular Cloning: A Laboratory Manual*, 1982) to promote fimbrial expression and grown overnight at 37° C. On the day of use, bacteria were scraped from the plate, resuspended in M9 medium (Maniatis, T. et al., *Molecular Cloning: A Laboratory Manual*, 1982) without amino acids, and shaken at 37° C. for 40 minutes to deplete cellular methionine stores. $^{35}$S-methionine (Trans$^{35}$S-label, 1137 Ci/mmol, ICN Biochemicals, Irvine, Calif.) was then added at 200 μCi per 10$^{10}$ organisms. The cells were shaken for one hour, washed three times in PBS and resuspended in PBS (pH 7.3), and counted in a scintillation counter to give a final activity of approximately 0.01 to 0.02 cpm/organism.

Bacterial Overlay Assays

Glycolipids (10 to 40 μg/lane) were chromatographed on glass HPTLC plates (Whatman) in CMW (50:40:10 by volume) with 0.05% CaCl$_2$ with one plate run in parallel for orcinol staining. Plates were dried, dipped for 1 minute in diethyl ether containing 0.5% polyisobutylmethacrylate, dried, and preincubated in 1% bovine serum albumin (BSA)/PBS for one hour, then washed three times in PBS. Radiolabelled bacteria were overlaid (10$^8$ cpm total per plate) and the plates were gently rocked for one hour, washed four times in PBS and subjected to autoradiography.

Antibody Overlay Assays and Radioimmunoassays of Glycolipids

Glycolipids separated on HPTLC were immunostained according to the procedure of Magnani et al. (Magnani, J. L. et al., *Anal Biochem.*, 109:399–402, 1980) as modified by Kannagi et al. (Kannagi, R. et al., *J. Biol. Chem.*, 257:14865–14872, 1982).

Radioimmunoassays of glycosphingolipids (GSL's) microtiter wells were performed according to the method of Karlsson (Karlsson, K.-A. et al., *Methods Enzymol.*, 138:220–232, 1987). Specificities and sources of MAbs are given in Table 1.

Samples of patients having a susceptibility to *E. coli* urinary tract infections, especially recurrent *E. coli* urinary tract infections, stained positive for Le$^a$ and SGG.

TABLE 1

| Specificities of Monoclonal Antibodies | | |
|---|---|---|
| Antigen | Monoclonal Antibody | Reference |
| Lewis$^a$ | CA3F4 | American Type Culture Collection |
| Sialosyl gal-globoside | ID4 | produced by conventional methods |
| Disialosyl I | NUH2 | Nudelman, E. D. et al., J. Biol. Chem., 264:18719–18725, 1989 |
| A type I, II, III | AH16 | Abe, K. et al., J. Immunol., 132:1951–1954, 1984 |
| A type III, IV | HH5 | Bremer, E. G. et al., J. Biol. Chem., |

TABLE 1-continued

Specificities of Monoclonal Antibodies

| Antigen | Monoclonal Antibody | Reference |
|---|---|---|
| Rabbit 1A | CRL1760 | 259:14773-14777, 1984* American Type Culture Collection |

*monoclonal antibody (MAb) HH5 has the same antigenic specificity as MAb MBr1, described in the reference.

Immunofluorescence Staining of Vaginal Epithelial Cells

Vaginal epithelial cells were washed three times in PBS (pH 7.3), counted in a hemocytometer, and approximately $3 \times 10^4$ cells were resuspended in PBS. Cells were incubated on ice or at room temperature with the primary MAb or no antibody for one hour, washed 3 times in PBS, and incubated with the FITC-conjugated secondary antibody (diluted 1:100) on ice for 30 minutes. Primary MAbs were undiluted ID4 or one of two control MAbs to unrelated antigens: NUH2 (undiluted) or CRL1760 (ATCC; undiluted). After 3 additional washes in PBS, stained cells were evaluated in a blinded fashion by examining each field sequentially using fluorescent microscopy then light microscopy. Cells with faint or no staining were scored as unstained and all others were considered positive.

Samples of patients having a susceptibility to *E. coli* urinary tract infections stained positive for SGG.

Using the above methods, the following experimentation was conducted.

Binding of *E. coli* R45 to Glycosphingolipid (GSL) Standards

The binding of metabolically radiolabelled *E. coli* strain R45 to glycolipid standards separated on HPTLC plates was determined using a broad panel of GSLs with varying carbohydrate moieties, as shown in Table 2. As predicted from its genotype and phenotype (P and F adhesin positive), the bacteria bound to globoseries GSLs containing the minimal pap-binding moiety gal $\alpha$1-4 gal as well as several of the suggested receptors for the F adhesin, including globoside, gal-globoside, the Forssman antigen, and globo A and H.

TABLE 2

Binding of *Escherichia coli* R45 to Glycosphingolipids (GSL's)

| Symbol | Structure | Binding |
|---|---|---|
| CMH | Glc$\beta$1—1cer | — |
| CDH | Gal$\beta$1-4Glc$\beta$1—1cer | — |
| CTM | Gal$\alpha$1-4Gal$\beta$1-4Glc$\beta$1—1cer | + |
| Globoside | GalNAc$\beta$1-3Gal$\alpha$1-4Gal$\beta$1-4Glc$\beta$1—1cer | + |
| Gal-globoside | Gal$\beta$1-3GalNAc$\beta$1-3Gal$\alpha$1-4Gal$\beta$1-4Glc$\beta$1—1cer | + |
| Forssman | GalNAc$\alpha$1-3Gal$\beta$1-3GalNAc$\beta$1-3Gal$\alpha$1-4Gal$\beta$1-4Glc$\beta$1—1cer | + |
| Globo H | (Fuc$\alpha$1-2)Gal$\beta$1-3GalNAc$\beta$1-3Gal$\alpha$1-4Gal$\beta$1-4Glc$\beta$1—1cer | + |
| Globo A | GalNAc$\alpha$1-3(Fuc$\alpha$1-2)Gal$\beta$1-3GalNAc$\beta$1-3Gal$\alpha$1-4Gal$\beta$1-4Glc$\beta$1—1cer | + |
| SGG | NeuAc$\alpha$2-3Gal$\beta$1-3GalNAc$\beta$1-3Gal$\alpha$1-4Gal$\beta$1-4Glc$\beta$1—1cer | + |
| DSGG | NeuAc$\alpha$2-3(NeuAc$\alpha$2-6)Gla$\beta$1-3GalNAc$\beta$1-3Gal$\alpha$1-4Gal$\beta$1-4Glc$\beta$1—1cer | + |
| ASGM1 | Gal$\beta$1-3GalNAc$\beta$1-4Gal$\beta$1-4Glc$\beta$1—1cer | — |
| ASGM2 | GalNAc$\beta$1-4Gal$\beta$1-4Glc$\beta$1—1cer | — |
| nLc6 | Gal$\beta$1-4GlcNAc$\beta$1-3Gal$\beta$1-4GlcNAc$\beta$1-3Gal$\beta$1-4Glc$\beta$1—1cer | — |
| B1 | Gal$\alpha$1-3(Fuc$\alpha$1-2)Gal$\beta$1-3GlcNAc$\beta$1-3Gal$\beta$1-4Glc$\beta$1—1cer | — |

Abbreviations:
CMH — ceramide trihexoside;
CDH — ceramide dihexoside;
CTH — ceramide trihexoside (globotriaosylceramide);
globoside — globotetrasylceramide;
gal-globoside — galactosyl globoside;
SGG — sialosyl gal-globoside;
DSGG — disialosyl gal-globoside;
ASGM1 — asialo GM1;
ASMG2 — asialo GM2;
nLc6 — lacto-N-norhexaosylceramide;
B1 — type 1 chain B antigen;
Glc — glucose;
cer — ceramide;
Gal — galactose;
GalNAc — N-acetylgalactosamine;
Fuc — fucose;
NeuAc — neuraminic acid;
GlcNAc — N-acetylglucosamine.

Binding of *E. coli* R45 to Glycolipids Extracted from Vaginal Epithelial Cells Total upper and lower phase GSLs were extracted from pooled vaginal epithelial cells collected from 3 groups of healthy college students: 10 nonsecretors (8 with a history of recurrent urinary tract infection and 2 without); 12 secretors with a history of recurrent urinary tract infection; and 18 secretors without recurrent infections. The distribution of ABO histo-blood group phenotypes among the patients in the groups was comparable. *E. coli* strain R45 (isolated from the urine of one of the patients with a urinary tract infection) was metabolically $^{35}$S-labelled as described above and reacted with the total upper and lower phase GSLs from each of the 3 groups of patients in bacterial HPTLC overlay assays as described above.

The organism bound to a unique glycolipid band in the total upper phase GSLs from nonsecretors which was not seen in GSLs from either group of secretors (data not shown). This experiment was repeated using pooled vaginal cells from 10 nonsecretors and 20 secretors (10 with and 10 without a history of recurrent urinary tract infection) with identical results. No differences in binding were detected in either experiment when secretors with and without a history of recurrent urinary tract infection were compared.

Subsequent experiments were conducted to identify the unique *E. coli*-binding GSL band detected in nonsecretors' vaginal epithelial cells. Total upper neutral GSLs and total upper gangliosides were extracted from vaginal epithelial cells pooled in equal quantities from 5 nonsecretors and 9 secretors and reacted with radiolabelled *E. coli* R45. The results are shown in FIGS. 1A and 1B.

FIG. 1A shows a representative autoradiogram of bacterial binding to GSLs extracted from equal quantities of pooled vaginal epithelial cells from 5 nonsecretors and 9 secretors and to GSL standards. An orcinol-stained HPTLC of the samples is shown in FIG. 1B.

Lane 1 contains ceramide trihexoasyl and globoside standards;

Lane 2 contains total lower phase GSLs from the nonsecretors;

Lane 3 contains total lower phase GSLs from the secretors;

Lane 4 contains the Forssman antigen standard;

Lanes 5 and 6 contain total upper neutral GSLs from nonsecretors and secretors, respectively;

Lanes 7 and 10 contain gal-globoside, sialosyl gal-globoside, and disialosyl gal-globoside standards;

Lanes 8 and 9 contain total upper phase gangliosides from nonsecretors and secretors, respectively.

In total ganglioside fractions from nonsecretors, but not from secretors, the organism bound to bands co-migrating with SGG and DSGG standards and also reacted with the standards themselves (FIG. 1A). The total amount of glycolipid placed in each lane was normalized based upon equivalent numbers of cells. As can be seen from the orcinol TLC, the chemical amounts of total upper phase gangliosides from nonsecretors and secretors are visually comparable (FIG. 1B, Lanes 8 and 9).

Immunostaining and Radioimmunoassays of Glycolipids Extracted from Pooled Vaginal Epithelial Cells To confirm the identity of SGG in the total upper ganglioside fraction from nonsecretors' vaginal epithelial cells, bands co-migrating with SGG and DSGG were eluted from HPTLC plates, chromatographed along with total gangliosides from nonsecretors and secretors, and reacted with MAb ID4 directed against SGG.

Figure 2:
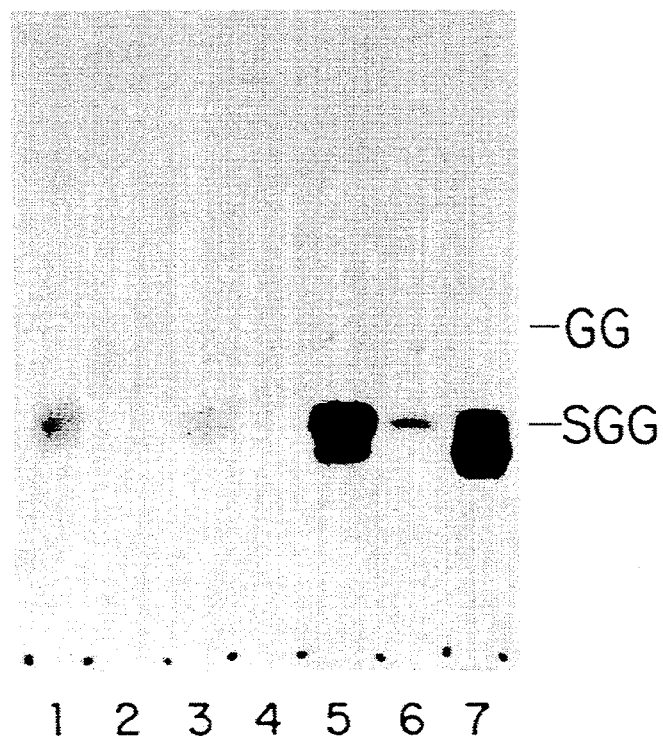
FIG. 2 depicts immunostaining of glycolipids extracted from pooled vaginal epithelial cells of nonsecretors and secretors.

The results are shown in FIG. 2 in which Lanes 1 and 2 contain total gangliosides from nonsecretors and secretors, respectively. Lane 3 contains the eluted band from nonsecretors which co-migrated with SGG and Lane 4 contains the eluted band from nonsecretors which co-migrated with DSGG. Lanes 5 and 7 contains SGG standards from human pancreas and Lane 6 contains gal-globoside standard from human pancreas (note trace of SGG).

As shown in FIG. 2, the MAb stained a band co-migrating with SGG in Lane 1, containing the total upper ganglioside fraction from nonsecretors and, in Lane 3, containing the putative SGG eluted from the nonsecretors. No staining was seen in the total ganglioside fraction from the secretors (Lane 2) nor in the putative DSGG material from the nonsecretors (Lane 4).

Figure 3:
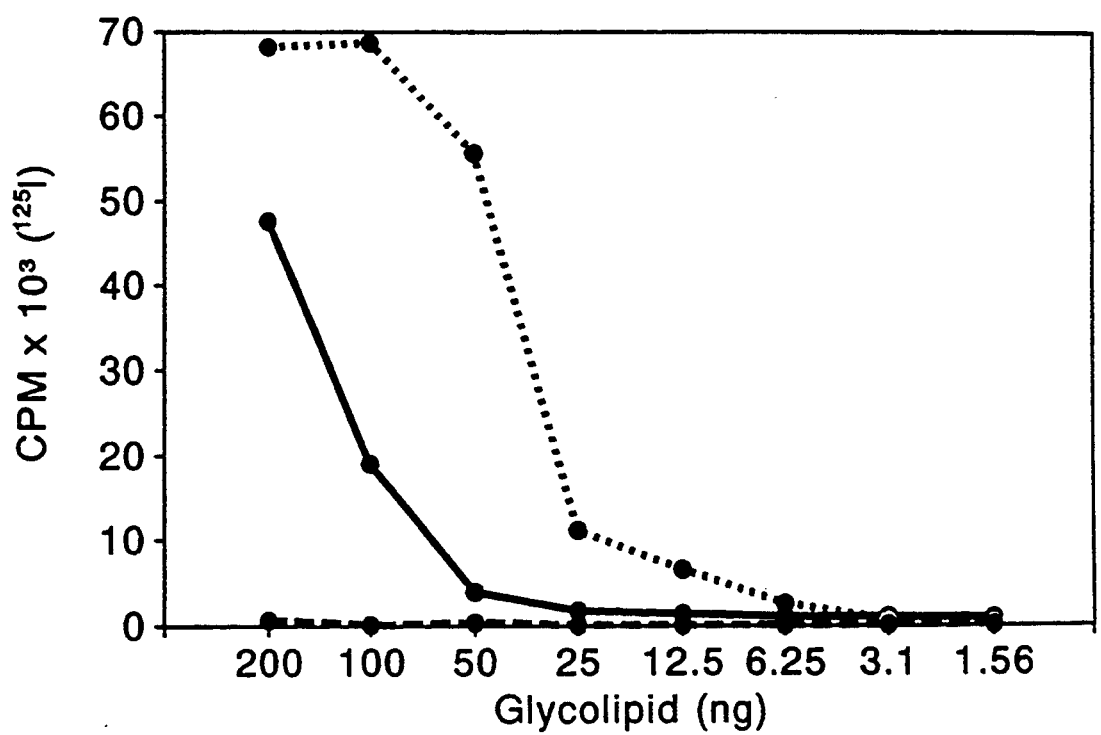
FIG. 3 shows the results of a radioimmunoassay which used a monoclonal antibody to SGG to assay glycolipids from nonsecretors. The dotted line indicates SGG standard from human pancreas. The solid line indicates band co-migrating with SGG eluted from TLC of nonsecretors' extracted vaginal epithelial cells. The dashed line indicates eluted band co-migrating with DSGG from nonsecretors and the following GSL standards: gal-globoside and DSGG from human pancreas, GD1a from bovine brain, and disialosyl I from human placenta.

The SGG and DSGG bands from the nonsecretors' vaginal epithelial cell extracts were then reacted with ID4 in a radioimmunoassay, shown in FIG. 3.

In FIG. 3, the dotted line indicates sialosyl gal-globoside (SGG) standard from human pancreas; the solid line indicates the band co-migrating with SGG eluted from TLC of nonsecretors' extracted vaginal epithelial cells; the dashed line indicates eluted band co-migrating with DSGG from nonsecretors and the following GSL standards: gal-globoside and DSGG from human pancreas, GD1a from bovine brain, and disialosyl I from human placenta.

FIG. 3 shows that the antibody reacted with the SGG band from nonsecretors and with the SGG standard but did not bind to the nonsecretor DSGG band nor to the DSGG, gal-globoside, GD1a, or disialosyl I standards.

To determine if the nonsecretor phenotypes of the patients as determined by blood and saliva testing was also expressed in vaginal epithelial cells, total upper phase GSLs from nonsecretors were chromatographed and reacted with MAbs "anti $Le^a$" and AH16 (against A type I, II and III). In the nonsecretor GSLs, a band co-migrating with $Le^a$ standard was brightly stained but no staining was observed with MAb AH16 (data not shown). In addition, MAbs against CTH and globoside/gal-globoside stained the cell extracts, confirming that globoseries GSLs are expressed in vaginal epithelial cells (data not shown).

Immunostaining of Glycolipids Extracted from Vaginal Epithelial Cells from Individual Patients To determine whether SGG is found in all nonsecretors (and is absent in all secretors) or present only in some nonsecretors, the total upper and lower phase GSLs were extracted from vaginal epithelial cells collected from 5 separate nonsecretor individuals as well as from 5 separate secretor individuals. Equal quantities of cells ($10^7$ cells/patient) were extracted and chromatographed as described and reacted with antibodies ID4 (against SGG) and HH5 (against A type III, IV). The secretor, ABO and $Le^a$ red blood cell phenotypes of the patients (determined by hemagglutination assays) are given in Table 3.

TABLE 3

Secretor, $Lewis^a$ and ABO Phenotypes and Antibody Binding

| Patient No. | Secretor Phenotype | ABO Phenotype | $Lewis^a$ Phenotype | Antibody Binding HH5 | ID4 |
|---|---|---|---|---|---|
| 1 | Nonsecrotor (NS) | A | + | − | + |
| 2 | NS | O | + | − | + |
| 3 | NS | O | + | − | + |
| 4 | NS | A | + | − | + |
| 5 | NS | B | + | − | + |
| 6 | Secretor (S) | O | − | − | − |
| 7 | S | O | − | − | − |
| 8 | S | AB | − | + | − |
| 9 | S | AB | − | + | − |
| 10 | S | A | − | + | − |

Figure 4:
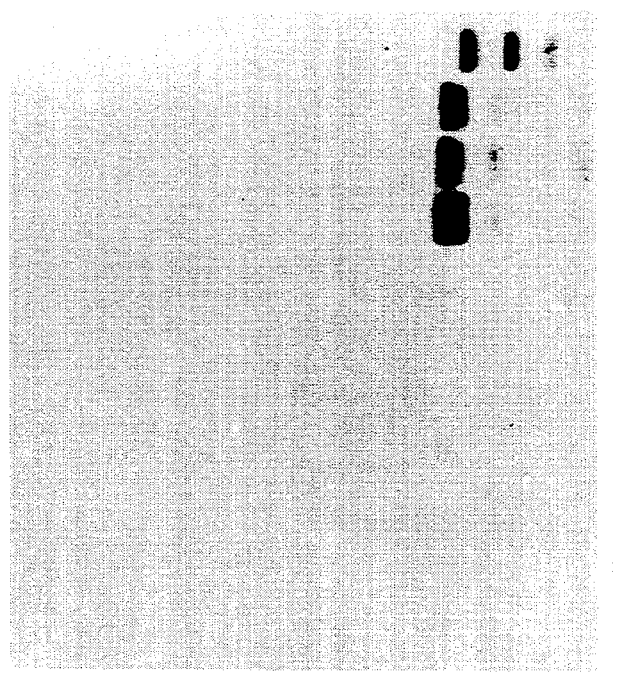
FIGS. 4A and 4B depict immunostaining of glycolipids extracted from vaginal epithelial cells of individual nonsecretors and secretors by autoradiographs from antibody overlay assays.

The results are shown in FIG. 4, wherein Lanes 1–10, contain samples in sequence from patients 1 to 10. Lane 11 in FIG. 4A contains SGG standard from human pancreas and in FIG. 4B contains upper neutral GSLs from type A human red blood cells.

As shown in FIG. 4A, SGG was detected in total upper phase GSLs from each of the 5 nonsecretors (Lanes 1-5), but not from any of the secretors Lanes 6-10).

In FIG. 4B, MAb HH5 detected A-reactive substances in GSLs from the three secretors with A or AB phenotypes (Lanes 8, 9 and 10) but not from the nonsecretors (Lanes 1-5).

Immunofluorescence Assays with Native Vaginal Epithelial Cells

Figure 5:
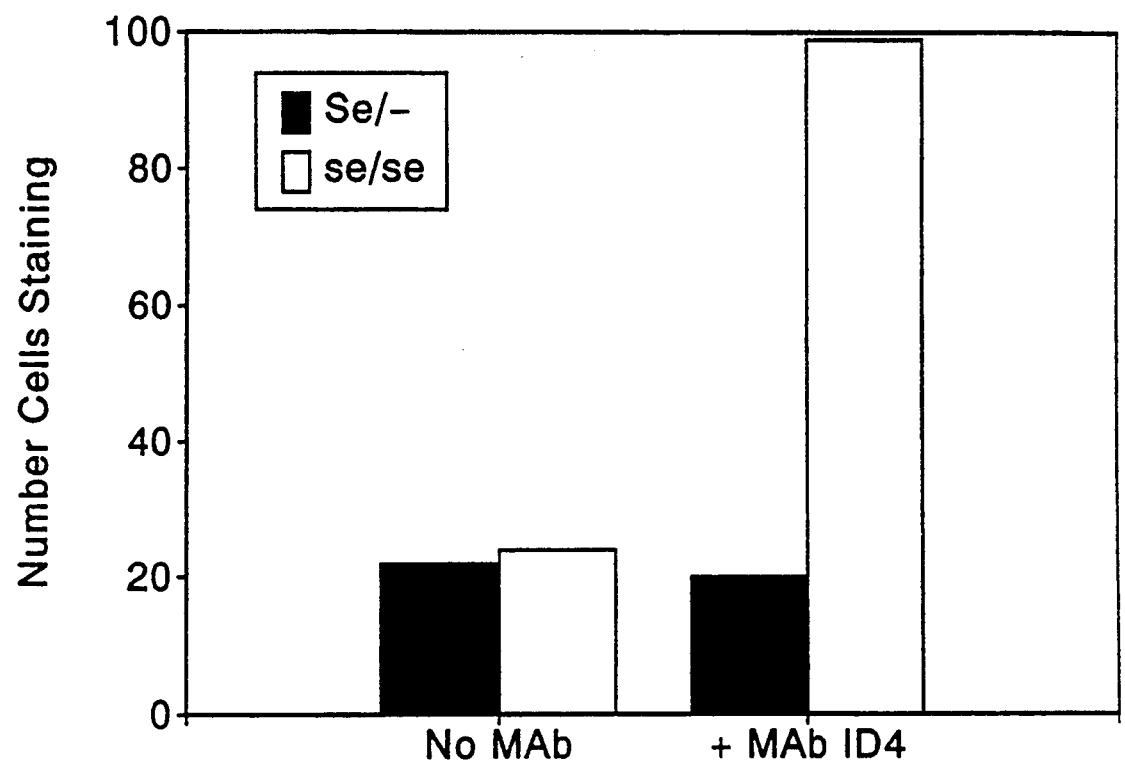
FIG. 5 is a bar graph depicting the degree of immunofluorescent staining of vaginal epithelial cells collected from individual nonsecretors and secretors and stained with a monoclonal antibody (MAb) to SGG.

To demonstrate that SGG is present and accessible on the surface of native vaginal epithelial cells from nonsecretors, but not secretors, immunostaining of cells from 2 individual secretors and 2 nonsecretors in three trials using MAb ID4 was compared. The results for the total number of cells stained in the three assays combined are shown in FIG. 5. Cells with faint or no staining were considered negative while any other degree of staining was considered positive.

As shown in FIG. 5, the majority of nonsecretors' vaginal epithelial cells were stained, while little or no staining of secretors' cells was observed. Staining of cells from both patient groups with control MAbs NuH2 and CRL1760 (against unrelated antigens) was comparable and minimal.

The above experiments demonstrate binding moieties unique to nonsecretors with structures consistent with Se gene-mediated control of antigen expression in globoseries GSLs from vaginal epithelial cells. SGG and DSGG were detected in extracts of aliquoted vaginal epithelial cells pooled from a total of 10 nonsecretors and also in cells collected and separately extracted from 5 additional individuals with the se/se phenotype, suggesting that the expression this antigen is uniform for nonsecretors. Considering all bacterial binding experiments using both pooled and individuals' vaginal epithelial cells, a total of 35 secretors' and 15 nonsecretors' epithelial cells were studied. The data supports the hypothesis that the Se locus controls the expression of ABO blood group antigen variants of globoseries GSLs in vaginal epithelial cells, an anatomic site which plays an important role in the sequence of colonization events preceding the development of urinary tract infection in women.

As described above, several globoseries GSLs are known receptors for uropathogenic *E. coli* and are present in other urinary tract sites (Lund, B. et al., *Mol. Microbiol.*, 2:255-263, 1988; Kallenius, G. et al., *FEMS Microbiol Lett.*, 7:297-302, 1980; Leffler, H. et al., *FEMS Microbiol. Lett.*, 8:127-134, 1980; Svanborg-Eden, C. et al., *Scand. J Infect Dis. Suppl.*, 24:144-147, 1980; Kallenius, G. et al., *Infection*, 8 (Suppl. 3):S288-S293, 1981; Kallenius, G. et al., *Lancet*, 2:604-606, 1981; Leffler, H. et al., *Infect Immun.*, 34:920-929, 1981; Kallenius, G. et al., *Scand. J. Infect. Dis. Suppl.*, 33:52-60, 1982; Svenson, S.B. et al., *Infection*, 11:73/61-79/67, 1983; Bock, K. et al., *J. Biol Chem.*, 260:8545-8551, 1985; Lindstedt, R. et al., *Infect. Immun.*, 57:3389-3394, 1989; Karr, J.F. et al., *Infect Immun.*, 58:4055-4062, 1990; Stromberg, N. et al., *EMBO J.*, 9:2001-2010, 1990; Breimer, M.E. et al., *J. Biochem.*, 98:1169-1180, 1985; Lindstedt, R. et al., *Infect. Immun.*, 59:1086-1092, 1991), but the influences of the Se gene on globoseries biosynthesis in vaginal epithelium has not been previously been known to have been demonstrated. One study suggested that globoseries GSL synthesis in voided uroepithelial cells from adults depended on ABO and secretor status (Leffler, H. et al., *In Host Parasite Interactions in Urinary Tract Infections*, 93-99, 1989). The presence of SGG and DSGG in uroepithelial cells from nonsecretors may account for the increased binding of *E. coli* to their cells and for their increased susceptibility to recurrent urinary tract infection.

In addition to supporting the role of a genetic host factor in the pathogenesis of recurrent urinary tract infection in women, the data of the present invention clarifies the mechanism by which this occurs.

Others have speculated that *E. coli* receptors on uroepithelial cells from nonsecretors are more accessible because of the lack of fucosyl transferase-mediated synthesis of A, B and H antigens, whereas in secretors, the presence of histo-blood group antigens on epithelial cells might shield the receptors and prevent bacterial binding (Sheinfeld, J. et al., *N. Engl. J. Med.*, 320:773-777, 1989; Lomberg, H. et al., *Infect. Immun.*, 51:919-926, 1986; Schoolnik, G.K., *New Engl. J. Med.*, 320:804-805, 1989). However, reports correlating secretor status with the expression of histo-blood group antigens on Type I-IV carbohydrate core structures in the urinary tract are conflicting (Orntorft, T.F. et al., *Lab. Invest.*, 58:576-583, 1988). The correlation of secretor state with expression of ABH antigens has only been clearly demonstrated for antigens carried on Type I chains (Leffler, H. et al., *In Host Parasite Interactions in Urinary Tract Infections*, 93-99, 1989; Orntorft, T.F. et al., *Lab. Invest.*, 58:576-583, 1988), but uropathogenic *E. coli* have not been reported to bind to Type I core GSLs (Leffler, H. et al., *In Host Parasite Interactions in Urinary Tract Infections*, 93-99, 1989).

This was also found to be true by the present inventors. In GSLs extracted from vaginal epithelial cells from nonsecretors and secretors, respectively, the present inventors identified major bands corresponding in TLC migration to Lewis$^a$ and Lewis$^b$ antigens. In extracts from nonsecretors, the Le$^a$ band reacted with a MAb directed to Le$^a$. However, *E. coli* did not bind to either of the Lewis$^a$ or Lewis$^b$ bands. In contrast, the present inventors have shown that on vaginal epithelial cells, there is a correlation between secretor status and ABH antigen expression of well-described receptors for uropathogenic *E. coli*, the Type IV chain (globoseries) GSLs. Rather than failing to shield bacterial receptors, nonsecretors synthesize unique sialylated, *E. coli* binding derivatives of the globoseries GSLs.

Genetic variability in glycosylation encoded by blood group genes is generally thought to be involved in "masking" or shielding glycan receptors for microbial pathogens. Globoseries GSLs characterized by a terminal or internal galactose alpha 1-4 galactose moiety are preferred receptors for *E. coli* adhesins. Previous studies have clearly shown that the binding of *E. coli* to globoseries GSLs changes when the disaccharide receptor site is further modified by elongation of the saccharide chain (Bock, K. et al., *J. Biol Chem.*, 260:8545-8551, 1985). The genetic variability inherent to blood group antigens implies that a proportion of the population lacks certain glycan structures. In such persons, competition for terminal glycosylation of the precursor gal-globoside is shared by both a fucosyltransferase and a sialyltransferase. Apparently, the affinity of the fucosyltransferase for the terminal galactose is greater and hence the Globo H structure is synthesized to the exclusion of any terminally sialylated structures. In contrast, nonsecretors lack such a fucosyltransferase and synthesize SGG and DSGG in epithelial cells through sialylation of the precursor gal-globoside, with no competition for terminal fucosylation by the absent Se gene-encoded fucosyltransferase. As evidenced by the results of the experimentation leading to the present invention, this sialylation does not interfere with the receptor activity of the globo core.

In summary, the present inventors have shown that nonsecretors of histo-blood group antigens synthesize unique GSLs, SGG and DSGG, on their vaginal epithelial cells which are not found in cells from secretors. As these moieties serve as receptors for uropathogenic *E. coli*, this finding provides a biochemical explanation for the increased adherence of bacteria to these women's uroepithelial cells and for their propensity to develop recurrent urinary tract infection. The present inventors have also shown that other globoseries GSLs known to be receptors for uropathogenic *E. coli* are present in GSL extracts from vaginal epithelial cells and bind bacteria in HPTLC overlay assays. In nonsecretors, SGG and DSGG may be more abundant or accessible on vaginal epithelial cells than other *E. coli* receptors, or the affinity of bacterial binding for these moieties may be higher than the affinity for other globoseries GSLS. Sialylation may alter the conformation of the adhesin binding site in favor of increased bacterial binding to SGG and DSGG as compared with binding to other available receptors.

Method for Determining Susceptibility to *E. coli* Urinary Tract Infections

Accordingly, the present invention provides a method for determining susceptibility to *E. coli* urinary tract infection comprising assaying a sample of epithelial cells for the presence or absence of at least one of $Le^a$, SGG, DSGG and an extended globo structure carrying the same terminal epitopes as $Le^a$, SGG, or DSGG or assaying a sample of vaginal secretions for the presence or absence of at least one of SGG or DSGG, and detecting the presence or absence of the at least one of $Le^a$, SGG, DSGG and the extended globo structure.

In the method for determining susceptibility to *E. coli* urinary tract infections, the assay is conducted by first collecting epithelial cells or vaginal secretions, with the secretions constituting the first supernatant sample from washing the cells, from a patient and preparing glycolipids as described above.

The epithelial cells which can be collected include uroepithelial cells, vaginal epithelial cells and buccal epithelial cells.

The glycolipid samples can be assayed for $Le^a$ and/or SGG by any known immunoassay method, preferably by an immunoblot assay, more preferably by an antibody overlay assay, a bacterial overlay assay and/or a radioimmunoassay.

When an antibody or bacterial overlay assay is used, the bacteria can be labelled as described above and the antibody can be labelled according to known methods. The bacterial overlay assay and/or antibody overlay assay can be conducted as described above.

When a radioimmunoassay is used, the radioimmunoassay can be conducted as described above.

Any appropriate monoclonal antibodies can be used. These monoclonal antibodies are either publicly available or can be produced by conventional methods. Preferably a panel of monoclonal antibodies can be used in the assay as set forth in Table 1 above, that is, CA3F4, ID4, NUH2, AH16, HH5, and CRL1760. CA3F4 and CRL1760 are available from the American Type Culture Collection. The other preferred monoclonal antibodies can be produced by conventional methods.

Detecting the presence of $Le^a$, SGG, DSGG, and an extended globo structure carrying the same terminal epitopes as $Le^a$, SGG, or DSGG after assaying can be conducted in accordance with appropriate methods known in the art.

Samples of patients having a susceptibility to *E. coli* urinary tract infections, especially recurrent *E. coli* urinary tract infections, will stain positive for $Le^a$, SGG, DSGG and the extended globo structure carrying the same terminal epitopes as $Le^a$, SGG, or DSGG.

Methods for Diagnosing Secretors and Nonsecretors of Histo-Blood Group Antigens

The present invention also provides a method for diagnosing secretors and nonsecretors of histo-blood group antigens comprising assaying a sample of vaginal epithelial cells, vaginal secretions or buccal epithelial cells for the presence or absence of at least one of SGG and DSGG, and detecting the presence or absence of the at least one of SGG and DSGG.

In the method for diagnosing nonsecretors and secretors of histo-blood group antigens based on the presence of SGG and/or DSGG, the assay is conducted by first collecting vaginal epithelial cells, vaginal secretions or buccal epithelial cells from a patient.

The cells or secretions can be treated in accordance with any known method in preparation for assaying depending on the assay method to be used. Preferably, the cells or secretions are treated in accordance with the method outlined above in preparation for immunofluorescence staining, with the secretions constituting the first supernatant sample from washing the cells.

The samples can be assayed for SGG and/or DSGG by any known immunoassay method. Preferably, immunofluorescence or a colorimetric ELISA method is used.

Any appropriate monoclonal antibody known in the art can be used. These monoclonal antibodies can be produced by conventional methods. Preferably, MAb ID4, which can be prepared by conventional methods, is used. Also, an antibody against stage-specific embryonic antigen-4 (SSEA-4), which is presumed to have the same structure as SGG, is expected to be used for detecting SGG and is known as MC813-70. MC813-70 can be produced by conventional methods. Stage-specific embryonic antigens (SSEA-3 and SSEA-4) are epitopes of a unique globo-series ganglioside isolated from human teratocarcinoma cells. *Embo J.*, Vol. 2, pages 2355-2361, 1983. Appropriate Mabs for DSGG can also be made by conventional methods.

Detecting the presence or absence of SGG and/or DSGG after assaying can be conducted in accordance with appropriate methods known in the art. When the detection is based on immunostaining of the cells, cells of nonsecretors will be stained, whereas little or no staining will occur in cells of secretors.

The present inventor further provides a method for diagnosing secretors of histo-blood group antigens comprises assaying a sample of vaginal epithelial cells or vaginal secretions for the presence or absence of at least one of globo H, globo ABO and lacto ABO, and detecting for the presence or absence of the at least one of globo H, globo ABO and lacto ABO.

In the method for diagnosing secretors of histo-blood group antigens based on the presence of globo H, globo ABO and lacto ABO, the assay is conducted by first collecting vaginal cells and/or secretions from a patient.

The cells and/or secretions are treated in accordance with any known methods in the art in preparation for assaying depending on the assay method to be used. Preferably, the cells and/or secretions are treated in accordance with the method outlined above in preparation for immunofluorescence staining, with the secretions constituting the first supernatant sample from washing the cells.

The samples can be assayed for globo H, globo ABO and/or lacto ABO by any known immunoassay method. Preferably, immunofluorescence or a colorimetric ELISA assay is used.

Any appropriate monoclonal antibody known in the art can be used and can be produced by conventional methods.

Detecting the presence or absence of globo H, globo ABO and/or lacto ABO after assaying can be conducted in accordance with appropriate methods known in the art. When the detection is based on immunostaining of the cells, cells of secretors will be stained, whereas little or no staining will occur in cells of nonsecretors.

Medicament for Preventing *E. coli* Urinary Tract Infections

The present invention further provides a medicament comprising a biologically effective amount of at least one bacterial receptor analogue, and a pharmaceutically acceptable diluent, carrier or excipient.

Preferably, the at least one bacterial receptor analogue is a stabilized synthetic carbohydrate. More preferred bacterial receptor analogues include carbohydrates having thioglycosides, N-trifluoroacetyl- or N-carbamyl-sialic acid, and replacement of O with S in hexose ring structures.

The at least one bacterial receptor analogue can be an analogue of bacterial receptors including galactosyl-globoside, SGG, DSGG or globo H.

The bacterial receptors used in the present invention can be prepared by methods which are known in the art.

The bacterial receptor analogues can be prepared by methods which are known in the art.

The biologically effective amount of the medicament according to the present invention can be determined using art-recognized methods, such as by establishing dose response curves in suitable animal models and extrapolating to humans; extrapolating from in vitro data; or by determining effectiveness in clinical trials.

Suitable doses of the receptor analogue according to the present invention depend upon the particular medical application, the severity of the condition, the half-life in circulation, etc., and can easily be determined by the skilled artisan.

The number of doses, daily doses and course of treatment may vary from individual to individual.

Depending on the particular medical application, the medicament can be administered in a variety of ways such as orally and topically. Also, the medicament can be administered in a spermicidal preparation.

The selection of suitable pharmaceutically acceptable carriers, diluents or excipients which can be used in the medicament for administration depends on the particular medical use and can be determined readily by the skilled artisan.

The medicament can take a variety of forms, such as tablets, capsules, bulk or unit dose powders or granules; may be contained with liposomes; or may be formulated into solutions, emulsions, suspensions, ointments, pastes, creams, jells, foams or jellies and the like.

Additionally, a variety of art-recognized carriers, excipients, diluents, fillers, etc., are likely to be included in the dosage forms. Such subsidiary ingredients include disintegrants, binders, lubricants, surfactants, emulsifiers, buffers, moisturizers, solubilizers and preservatives. The artisan can configure the appropriate formulation comprising the compound seeking guidance from numerous authorities and references such as Goodman et al., Goodman & Gilman's, *The Pharmaceutical Basis of Therapeutics*, 6th Ed., 1980.

Method for Preventing *E. coli* Urinary Tract Infections

The present invention further provides a method for preventing *E. coli* urinary tract infection comprising administering to a host a biologically effective amount of at least one *E. coli* bacterial receptor or bacterial receptor analogue.

The at least one bacterial receptor can include galactosyl-globoside, SGG, DSGG and globo H and can be prepared in accordance with methods known in the art.

The at least one bacterial receptor analogue is as described for the medicament.

The bacterially effective amount can be determined as described above for the medicament.

The method is especially useful for preventing recurrent *E. coli* urinary tract infections.

EXAMPLES

The invention will now be described by reference to specific examples, which are merely exemplary and are not considered to limit the invention.

Example 1

Assay for Determining Susceptibility to *E. coli* Urinary Tract Infection

Vaginal epithelial cells were collected from a patient population by saline rinsing and gentle scraping. The cells were washed 4 times in phosphate buffered saline (PBS), pH 7.3 and were stored in a freezing medium (85% M199 (Sigma), 10% fetal calf serum, 5% DMSO) at −70° C. until use. Prior to glycolipid extraction, the cells were washed 4 times in PBS, quantitated in a hemocytometer and equalized for extraction procedures. The total upper and lower phase glycolipid fractions were obtained as follows: cells were extracted twice with 10 volumes isopropanol:hexane:water (IHW) (55:25:20 by volume) with sonication in a warm bath and centrifugation at 2,500 RPM for 10 minutes. The combined supernatants were dried under nitrogen and twice resuspended in chloroform: methanol (CM) (2:1 by volume) with one-sixth volume water, inverted 20 times, and centrifuged at 2,000 RPM for 10 minutes. Total upper and lower phases were then evaporated under nitrogen stream and resuspended in IHW for chromatography.

For separation of total upper neutral glycolipids and gangliosides, upper phase glycolipids were first resuspended in 0.1% KCl in water, subjected to C18 Sep-Pak reverse phase column chromatography, washed with water, eluted with methanol, dried, and passed over a DEAE Sephadex A-25 column. Gangliosides were then eluted with 0.45M ammonium acetate in methanol, dried, and passed over a C18 column.

Glycolipids were preparatively separated by chromatography on glass HPTLC plates (Whatman) in chloroform:methanol:water (CMW) 50:40:10 with 0.05% $CaCl_2$. The bands were visualized with primuline under UV light, marked with a pencil, scraped from the silica plates, extracted twice in IHW, and dried.

The glycolipid samples were then assayed for the presence of $Le^a$ and SGG by antibody overlay assays and radioimmunoassay methods described above using a panel of MAbs set forth in Table 1.

Immunostaining was evaluated. Samples of patients having a susceptibility for *E. coli* urinary tract infections stained positive for $Le^a$ and SGG.

Example 2

Assay for Determining Nonsecretors and Secretors of Histo-Blood Groug Antigens

Vaginal epithelial cells were collected from patients having secretor status and nonsecretor status with saline and gentle scraping with a spatula to obtain cell samples. (Secretor status and nonsecretor status were determined beforehand by using a hemagglutination inhibition assay performed on saliva.) These cells were washed three times in PBS (pH 7.3), counted in a hemocytometer, and approximately $3 \times 10^4$ cells were resuspended in PBS.

The samples were then assayed by immunofluorescence using MAb ID4 to detect the presence of SGG by incubating the cells on ice or at room temperature with the primary MAb ID4 for one hour, washed 3 times in PBS, and incubated with the FITC-conjugated secondary antibody (diluted 1:100) on ice for 30 minutes. After 3 additional washes in PBS, stained cells were evaluated in a blinded fashion by examining each field sequentially using fluorescent microscopy then light microscopy.

Immunostaining was then evaluated. Cells with faint or no staining were scored as unstained and all others were considered positive.

Samples of patients having nonsecretor status stained positive for SGG.

Example 3

Assay for Determining Secretors of Histo-Blood Group Antigens

Vaginal epithelial cells were collected from patients having secretor status and nonsecretor status with saline and gentle scraping with a spatula to obtain cell samples. These cells were washed three times in PBS (pH 7.3), counted in a hemocytometer, and approximately $3 \times 10^4$ cells were resuspended in PBS.

The samples were then assayed by immunofluorescence using available MAbs to detect the presence of globo H, globo ABO and lacto ABO by incubating the cells on ice or at room temperature with the primary MAb for one hour, washing 3 times in PBS, and incubating with an FITC-conjugated secondary antibody (diluted 1:100) on ice for 30 minutes. After 3 additional washes in PBS, stained cells were evaluated in a blinded fashion by examining each field sequentially using fluorescent microscopy then light microscopy.

Immunostaining was then evaluated. Cells with faint or no staining were scored as unstained and all others were considered positive.

Samples of patients having secretor status stained positive for globo H, globo ABO and/or lacto ABO.

While the invention has been described in detail and with reference to specific embodiments thereof, it will be apparent to one skilled in the art that various changes and modifications can be made therein without departing from the spirit and scope thereof.

What is claimed is:

1. A method for determining susceptibility to *E. coli* urinary tract infection (IUTI) comprising:
   (a) assaying a sample of epithelial cells for the presence or absence of at least one of sialosyl galactosyl-globoside (SGG), disialosyl galactosyl-globoside (DSGG) and an extended globo structure carrying the same terminal epitopes as sialosyl galactosyl-globoside or disialosyl galactosyl-globoside, or assaying a sample of vaginal secretions for the presence or absence of at least one of sialosyl galactosyl-globoside or disialosyl galactosyl-globoside, and
   (b) detecting the presence or absence of the at least one of sialosyl galactosyl-globoside, disialosyl galactosyl-globoside and the extended globostructure; wherein presence of SGG, DSGG or extended globo structure carrying SGG and DSGG epitopes correlates with an increased susceptibility to UTI.

2. The method of claim 1, wherein the epithelial cells are selected from the group consisting of uroepithelial cells, vaginal epithelial cells and buccal epithelial cells.

3. The method of claim 1, wherein the assaying is performed by an assay selected from the group consisting of antibody overlay assays, bacterial overlay assay and radioimmunoassays.

4. The method of claim 1, wherein the *E. coli* urinary tract infection is recurrent.

5. A method for diagnosing secretors and nonsecretors of histo-blood group antigens comprising:
   (a) assaying a sample of vaginal epithelial cells, vaginal secretions or buccal epithelial cells for the presence or absence of at least one of sialosyl gal-globoside (SGG) and disialosyl gal-globoside (DSGG), and
   (b) detecting the presence or absence of the at least one of sialosyl gal-globoside and disialosyl gal-globoside; wherein SGG and DSGG is found in samples from nonsecretors.

6. The method of claim 5, wherein the assaying is performed by immunofluorescence or a colorimetric ELISA assay.

* * * * *

UNITED STATES PATENT AND TRADEMARK OFFICE
Certificate

Patent No. 5,374,532                                                              Patented: December 20, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ann Stapleton, Edward Nudelman, Sen-Itiroh Hakomori, Walter E. Stamm, Mark Stroud.

Signed and Sealed this Eighteenth Day of July, 2000.

<div style="text-align:right">

JAMES C. HOUSEL
*Supervisory Patent Examiner*
Technology Center 1600,
Biotechnology </div>